(12) United States Patent
Shariati et al.

(10) Patent No.: US 12,329,428 B2
(45) Date of Patent: Jun. 17, 2025

(54) MEDICAL DEVICE, SURGICAL KIT AND A METHOD FOR PERFORMING OSTEOTOMY

(71) Applicants: Mohammad Javad Shariati, Mashad (IR); Amir Reza Kachooei, Philadelphia, PA (US); Ahmadreza Afshar, Urmia (IR)

(72) Inventors: Mohammad Javad Shariati, Mashad (IR); Amir Reza Kachooei, Philadelphia, PA (US); Ahmadreza Afshar, Urmia (IR)

( * ) Notice: Subject to any disclaimer, the term of this patent is extended or adjusted under 35 U.S.C. 154(b) by 396 days.

(21) Appl. No.: 17/859,637

(22) Filed: Jul. 7, 2022

(65) Prior Publication Data

US 2023/0014382 A1 Jan. 19, 2023

Related U.S. Application Data

(60) Provisional application No. 63/221,305, filed on Jul. 13, 2021.

(51) Int. Cl.
*A61B 17/80* (2006.01)
*A61B 17/15* (2006.01)
(Continued)

(52) U.S. Cl.
CPC ........ *A61B 17/8061* (2013.01); *A61B 17/151* (2013.01); *A61B 2017/681* (2013.01); *A61B 17/7216* (2013.01); *A61B 17/7225* (2013.01); *A61B 17/8004* (2013.01); *A61B 17/8014* (2013.01); *A61B 17/8019* (2013.01); *A61B 17/8023* (2013.01); *A61B 17/8052* (2013.01);
(Continued)

(58) Field of Classification Search
CPC .............. A61B 17/8061; A61B 17/151; A61B 17/8004; A61B 17/8023; A61B 17/80; A61B 17/8014; A61B 17/8052; A61B 17/8057; A61B 17/808; A61B 17/7216; A61B 17/7225; A61B 17/8019; A61B 2017/564; A61B 2017/681; A61B 2090/061; A61B 90/06
USPC ..... 606/88, 280, 70, 71, 281, 282, 286, 291, 606/86 R, 87, 102, 105, 86 B, 902, 915
See application file for complete search history.

(56) References Cited

U.S. PATENT DOCUMENTS

| | | | | |
|---|---|---|---|---|
| 6,129,728 A | * | 10/2000 | Schumacher | ........ A61B 17/888 606/291 |
| 2004/0102778 A1 | * | 5/2004 | Huebner | ............ A61B 17/8033 606/71 |

(Continued)

*Primary Examiner* — Marcela I. Shirsat

(57) ABSTRACT

A surgical kit and a method for performing osteotomy is disclosed. The surgical kit comprises at least two lateral plates and a central plate. The two lateral plates are scaled and fixed over a surgical bone adjacent to each other with an exact distance measured by the scaled lateral plates while the central plate is over two lateral plates to maintain the alignment. The distance is equal to the shortening amount of bone based on the pre-operative measurements. The central plate slides laterally over the two lateral plates to expose the surgical site of the bone. Shortening osteotomy is performed to shorten the bone equal to the distance between the two lateral plates. The central plate then laterally slides over the two lateral plates to achieve the anatomic alignment. Further, the central plate and the two lateral plates are securely fixed to the bone using one or more fasteners.

10 Claims, 12 Drawing Sheets

(51) Int. Cl.
*A61B 17/68* (2006.01)
*A61B 17/72* (2006.01)
*A61B 90/00* (2016.01)

(52) U.S. Cl.
CPC ..... *A61B 17/8057* (2013.01); *A61B 2090/061* (2016.02)

(56) References Cited

U.S. PATENT DOCUMENTS

2006/0271052 A1* 11/2006 Stern .................. A61B 17/7059
606/283
2015/0313652 A1* 11/2015 Burckhardt ............. A24F 40/30
606/71

\* cited by examiner

MEDICAL DEVICE, SURGICAL KIT AND A METHOD FOR PERFORMING OSTEOTOMY

BACKGROUND OF THE INVENTION

A variety of surgical techniques, for example, osteotomy require bone cutting. The success of many of these surgical techniques can rely on the precision with which a cut is made. Further, certain surgical cuts require a series of parallel cuts. In particular, an osteotomy is a surgical procedure to cut a bone. After the bone is cut, it may be lengthened, straightened, or shortened during the surgery (acutely). In most cases, the osteotomy will involve the removal or realignment of a portion of bone in order to correct a problem that affects a patient's movement or unloading bones like in kienbock disease. However, it is often difficult for a surgeon to maintain a precise angular relationship between the cuts.

In general, malunion due to rotational/angular displacement after osteotomy's fixation remains a common complication in the treatment. Few existing systems could solve this problem by fixing the plate and screws before the osteotomy surgery and performing the osteotomy after removing the plate and screws. In another way, for example, in treatment of kienbock disease, the radius bone is pointed before performing the osteotomy in order to reach anatomic position after the osteotomy.

However, there is a complication that in second step, the screws could lose grip due to widening of holes in the first way. Further, after the osteotomy, there is a limitation that the second way could fail to actually make the points together. There is no exact way, however, pointing the bone in a conventional way. Yet, this is not accurate for avoiding of lower or higher amount of shortening or lengthening of the bone. Further, the existing systems may suffer from various inadequacies, such as lack of accuracy, flexibility and/or speed in guide positioning.

Henceforth, there is a need in the art for a medical device and method for precisely performing osteotomy surgery, whereby a bone is cut to accurately either shorten or lengthen it. This method could enable the surgeon to perform the osteotomy for accurately shortening the bone based on a pre-operative plan. The medical device and method could eliminate the limitations of malunion due to rotational or angular displacement after osteotomy's fixation.

SUMMARY OF THE INVENTION

The present disclosure discloses a method for performing shortening osteotomies in the long bones. The present disclosure further discloses a medical device or osteotomy device or surgical kit, as well as methods for precisely performing osteotomy surgery, whereby a bone is cut to accurately shorten its length. The surgical kit and method could enable the surgeon to perform the osteotomy for accurately and equally shortening the bone based on a pre-operative plan or intra-operative assessment.

In one embodiment, the surgical kit for performing osteotomy comprises at least two lateral plates and a central plate. In one embodiment, the at least two lateral plates include a first lateral plate and a second lateral plate. In one embodiment, the first lateral plate is configured to fix over a bone. In one embodiment, the first lateral plate comprises a top surface and a bottom surface. The top surface is configured to face away from the bone when implanted. The bottom surface is configured to be in contact with the bone when implanted.

In one embodiment, the first lateral plate further comprises a first proximal end and a first distal end aligned along a longitudinal axis of the bone. In one embodiment, the first lateral plate further comprises one or more through-holes on its surface configured to fix to the bone. In one embodiment, the first lateral plate further comprises at least one compression hole at the first proximal end and one or more locking holes. In one embodiment, the first lateral plate further comprises a first pair of tabs on both sides along its length.

In one embodiment, the second lateral plate is configured to fix over the bone adjacent to the first lateral plate. In one embodiment, the first lateral plate and the second lateral plate are fixed on the bone with an exact distance based on a pre-operative plan by locking screws while the central plate is over them to keep the alignment. In one embodiment, the distance between the first lateral plate and the second lateral plate is equal to the shortening amount of bone based on pre-operative measurements. In one embodiment, the second lateral plate comprises a top surface and a bottom surface. The top surface is configured to face away from the bone when implanted and the bottom surface is configured to be in contact with the bone when implanted.

In one embodiment, the second lateral plate further comprises a second proximal end and a second distal end aligned along a longitudinal axis of the bone. In on embodiment, the second lateral plate further comprises one or more through-holes on its surface configured to fix to the bone with one or more fasteners such as locking screws. The locking screws completely enter into the lateral plates, thereby allowing the central plate to slide on the fixed lateral plates. In on embodiment, the second lateral plate further comprises at least one compression hole at the second proximal end and one or more locking holes. In on embodiment, the second lateral plate further comprises a second pair of tabs on both sides along its length.

In one embodiment, the central plate is slidably placed over the first lateral plate and the second lateral plate. In one embodiment, the central plate has a top surface and a bottom surface. The top surface is configured to face away from the at least two lateral plates when implanted and the bottom surface is configured to be in contact with the at least two lateral plates when implanted.

In one embodiment, the central plate further comprises a first end and a second end aligned along a longitudinal axis of the bone. In one embodiment, the central plate has one or more through-holes on its surface configured to securely fix the at least two lateral plates to the bone via one or more fasteners after performing shortening osteotomy, exactly equal to distance between two fixed lateral plates which are fixed in distance together based on pre-operative planed amount of shortening. It allows an accurate amount of bone shortening and anatomical reduction and fixation of the osteotomy site. In one embodiment, the through-holes of the central plate and the at least two lateral plates are superimposed for final fixation in condition that there is no distance between two lateral plates. In one embodiment, the one or more fasteners are at least two cortical screws and one or more locking screws.

In one embodiment, the central plate further comprises at least two compression holes at its center and one or more locking holes proximal to the compression holes. In one embodiment, the central plate further comprises a channel on both sides along its length configured to slide laterally along the tabs of the at least two lateral plates.

In one embodiment, the present disclosure is a method for performing osteotomy using surgical kit that comprises at least two lateral plates and a central plate. In one embodiment, the at least two lateral plates that includes a first lateral plate and a second lateral plate. In one embodiment, the two lateral plates are adjacently fixed over a bone at a predefined distance. In one embodiment, the central plate is slidably placed over the two lateral plates configured to securely fix the two lateral plates to the bone using one or more fasteners.

In one embodiment, the method follows the following steps. At one step, the two lateral plates are placed over the bone at an exact equal to the shortening amount of osteotomy based on pre-operative planed amount of shortening to form a surgical site. In one embodiment, the at least two lateral plates are fixed to the bone via one or more locking holes using one or more fasteners in first distal end and second distal end while the central plate is placed over two lateral plates in the first proximal end and second proximal end to keep the anatomic alignment. In one embodiment, the first lateral plate has at least two locking holes at a first distal end and the second lateral plate has at least two locking holes at a second distal end. In one embodiment, the fasteners could be one or more cortical screws and one or more locking screws.

At another step, the central plate laterally slides over the two lateral plates configured to expose the surgical site of the bone in distance between two lateral plates. At another step, the surgical bone is shortened equal to the distance between the two lateral plates using the shortening osteotomy process, then two lateral plates will stick together longitudinally. In one embodiment, the distance between the first lateral plate and the second lateral plate is equal to the shortening amount of bone based on the pre-operative measurements and after osteotomy there will not be any distance between them.

At another step, the central plate slides laterally over the two lateral plates in the osteotomy site and is configured so as to fix the central plate and the two lateral plates to the bone using one or more fasteners by aligning the holes of the central plate and the two lateral plates. In one embodiment, the holes of the central plate and the holes of the two lateral plates are superimposed for final fixation. If the shortening osteotomy is performed enough, two lateral plates will reach together without distance so the holes will be superimposed with the central plate to the bone using one or more fasteners. In one embodiment, the one or more fasteners are at least two cortical screws for compression in the osteotomy site and one or more locking screws.

One aspect of the present disclosure is directed to a surgical kit for performing an osteotomy, comprising: (a) at least two lateral plates, including (i) a first lateral plate, (ii) a second lateral plate, and (b) a central plate. Before performing osteotomy, the first and second lateral plates are fixed on the bone while the central plate is placed over the two lateral plates to preserve the perfect anatomical alignment between the two lateral plates for measuring the exact distance between two lateral plates. The distance between the two lateral plates should be equal to the planned amount of bone shortening osteotomy.

In one embodiment, the first lateral plate is fixed over a bone having a top surface configured to face away from the bone when implanted, a bottom surface configured to be in contact with the bone when implanted, a first proximal end and a first distal end aligned along a longitudinal axis of the bone, wherein the first lateral plate has one or more through-holes on its surface configured to fix to the bone. In one embodiment, the second lateral plate fixed over the bone adjacent to the first lateral plate having a top surface configured to face away from the bone when implanted, a bottom surface configured to be in contact with the bone when implanted, a second proximal end and a second distal end aligned along a longitudinal axis of the bone, wherein the second lateral plate has one or more through-holes on its surface configured to fix to the bone. In one embodiment, the central plate slidably placed over the first lateral plate and the second lateral plate, wherein the central plate has a top surface configured to face away from the at least two lateral plates when implanted, a bottom surface configured to be in contact with the at least two lateral plates when implanted, a first end and a second end aligned along a longitudinal axis of the bone, wherein the central plate has one or more through-holes on its surface configured to securely fix the at least two lateral plates to the bone via one or more fasteners, thereby allowing an accurate amount of bone shortening and anatomical reduction and fixation of osteotomy site.

In one embodiment, the first lateral plate further comprises at least one compression hole at the first proximal end and one or more locking holes at the first distal end. In another embodiment, the first lateral plate further comprises a first pair of tabs on both sides along its length. In one embodiment, the second lateral plate further comprises at least one compression hole at the second proximal end and one or more locking holes at the second distal end. In another embodiment, the second lateral plate further comprises a second pair of tabs on both sides along its length. In one embodiment, the lateral plates are fixed on the bone by one or more locking screws to allow sliding of the central plate on them. After performing osteotomy, the central plate, is fixed to the bone over two lateral plates with at least two compression screws and at least two locking screws. In one embodiment, the central plate further comprises at least two compression holes at its center and one or more locking holes proximal and distal to the compression holes.

In one embodiment, the central plate further comprises a channel on both sides along its length configured to slide laterally along the tabs of the at least two lateral plates. In another embodiment, the first lateral plate and the second lateral plate are fixed on the bone with exact distance based on a pre-operative plan. In one embodiment, the distance between the first lateral plate and the second lateral plate is equal to the shortening amount of bone based on the pre-operative measurements. In another embodiment, the holes of the central plate and the at least two lateral plates are superimposed for final fixation. In one embodiment, the one or more fasteners are at least two cortical screws and two or more locking screws.

One aspect of the present disclosure is directed to a surgical kit for performing osteotomy, comprising (a) at least two lateral plates that includes (i) a first lateral plate fixed over a bone having a top surface configured to face away from the bone when implanted, a bottom surface configured to be in contact with the bone when implanted, a first proximal end and a first distal end aligned along a longitudinal axis of the bone, wherein the first lateral plate has one or more through-holes on its surface configured to fix to the bone, and (ii) a second lateral plate fixed over the bone adjacent to the first lateral plate having a top surface configured to face away from the bone when implanted, a bottom surface configured to be in contact with the bone when implanted, a second proximal end and a second distal end aligned along a longitudinal axis of the bone, wherein the second lateral plate has one or more through-holes on its surface configured to fix to the bone; and (b) a central plate slidably placed over the first lateral plate and the second lateral plate, wherein the central plate has a top surface configured to face away from the at least two lateral plates when implanted, a bottom surface configured to be in contact with the at least two lateral plates when implanted, a first end and a second end aligned along a longitudinal axis of the bone, wherein the two lateral plates are fixed on bone in anatomical alignment by the central plate, and the central plate is placed on the two lateral plates, thereby allowing the fixed lateral plates to preserve the anatomical alignment and measure the exact distance between two lateral plates. The distance between the two lateral plates should be equal to amount of bone shortening osteotomy, wherein the central plate has one or more through-holes on its surface configured to securely fix the at least two lateral plates to the bone at an exact distance equal to the amount of bone shortening osteotomy via one or more fasteners, thereby allowing an accurate amount of bone shortening and anatomical reduction and fixation of osteotomy site. In one embodiment, the first lateral plate further comprises one or more locking holes at the first distal end. In one embodiment, the second lateral plate further comprises one or more locking holes at the second distal end. In another embodiment, the second lateral plate further comprises a second pair of tabs on both sides along its length.

Another aspect of the present disclosure is directed to a method of performing osteotomy using a surgical kit having at least two lateral plates that include a first lateral plate and a second lateral plate, adjacently fixed over a bone at a pre-defined distance and a central plate slidably placed over the at least two lateral plates configured to securely fix the at least two lateral plates to the bone using one or more fasteners, comprising: (a) placing the at least two lateral plates over a bone at exact distance between them while central plate is over them to keep the anatomic alignment in longitudinal axis of the bone as a surgical site, wherein the at least two lateral plates are fixed to the bone via one or more locking holes in first distal end and second distal end using one or more fasteners; (b) sliding the central plate laterally over the at least two lateral plates configured to expose the surgical site of the bone, which is between first proximal end and second proximal end of lateral plates respectively; (c) performing shortening osteotomy equal to the distance between the two lateral plates; and (d) sliding the central plate laterally over the at least two lateral plates in the osteotomy site while making anatomical reduction in osteotomy site, then configured to fix the central plate and the at least two lateral plates to the bone using one or more fasteners by aligning the holes of the central plate and the at least two lateral plates. In one embodiment, there is complete overlap of the central plate and two lateral plates when there is no distance between the two lateral plates.

Another aspect of the present disclosure is directed to a method of performing osteotomy using a surgical kit having at least two lateral plates that include a first lateral plate and a second lateral plate, adjacently fixed over a bone at a pre-defined distance and a central plate slidably placed over the at least two lateral plates configured to securely fix the at least two lateral plates to the bone using one or more fasteners, comprising: (a) placing the at least two lateral plates over a bone at exact distance to form a surgical site, wherein the at least two lateral plates are fixed to the bone via one or more locking holes using one or more fasteners; (b) sliding the central plate laterally over the at least two lateral plates configured to expose the surgical site of the bone; (c) performing shortening osteotomy equal to the distance between the two lateral plates; and (d) sliding the central plate laterally over the at least two lateral plates in the osteotomy site configured to fix the central plate and the at least two lateral plates to the bone using one or more fasteners by aligning the holes of the central plate and the at least two lateral plates.

In one embodiment, the first lateral plate has at least two locking holes at a first distal end and the second lateral plate has at least two locking holes at a second distal end. In one embodiment, the distance between the first lateral plate and the second lateral plate is equal to the shortening amount of bone based on the pre-operative measurements. In another embodiment, the central plate slides over the first lateral plate and the second lateral plate, thereby allowing an accurate amount of bone shortening and anatomical reduction and fixation of osteotomy site. In one embodiment, the holes of the central plate and the at least two lateral plates are superimposed for final fixation.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

Figure 1:
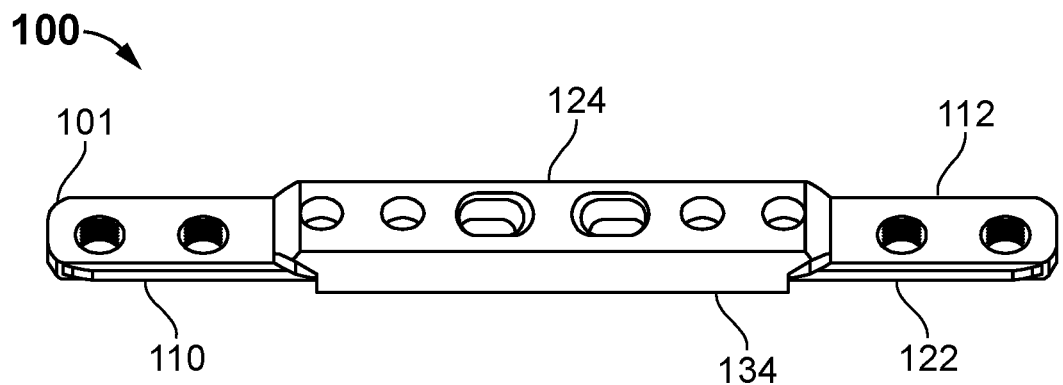
FIG. 1 exemplarily illustrates a perspective view of the surgical kit or medical device, according to an embodiment of the present disclosure.

The present disclosure generally relates to a medical device and method for precisely performing and fixing osteotomy surgery, whereby a bone is cut to accurately either shorten or lengthen it or to change its alignment. The medical device and method could enable the surgeon to perform the osteotomy procedure and accurately and equally shorten the bone based on a pre-operative plan with maintaining the anatomic alignment.

A description of embodiments of the present disclosure will now be given with reference to the figures. It is expected that the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes that come within the meaning and range of equivalency of the claims are to be embraced within their scope.

Before any embodiments of the invention are explained in detail, it is to be understood that the disclosure is not limited in its application to the details of construction nor to the arrangement of components set forth in the following description or illustrated in the drawings. The disclosure is capable of other embodiments and of being practiced or of being carried out in various ways.

The present disclosure discloses a medical device or osteotomy device or surgical kit for use in osteotomy or orthopedic surgery to keep the correct alignment of the bone or joint. In one embodiment, the present disclosure further discloses the surgical kit having one or more orthopedic plates with sliding ability after plate fixation to aid in the reduction of complications in the site of osteotomy.

Referring to FIG. 1, a perspective view of the surgical kit or medical device or osteotomy device 100, according to one embodiment is disclosed. In one embodiment, the surgical kit 100 is configured to enable a physician or a surgeon to precisely perform the osteotomy surgery, whereby a bone 140 (shown in FIG. 5) is cut to accurately shorten with maintained anatomical alignment based on pre-osteotomy fixation. In one embodiment, the surgical kit 100 permits the osteotomy with sliding ability to aid in the reduction of complications in a surgical site 136 (shown in FIG. 5) of osteotomy, after plate fixation like over-shortening or mal-reducted osteotomy. In one embodiment, the surgical kit 100 comprises at least two lateral plates and a central plate 124.

The at least two lateral plates include a first lateral plate 101 and a second lateral plate 112. In one embodiment, the central plate 124 is provided with channels or grooves 134 on both sides. In one embodiment, the channels or grooves 134 of the central plate 124 is designed and configured to slide over the lateral plates (101 and 112) via the first pair of tabs or rails 110 and second pair of tabs or rails 122, respectively. In one embodiment, the central plate 124 could be moved to accurately perform the osteotomy surgery for shortening of the bone 140 between the two lateral plates (101 and 112).

Figure 2:
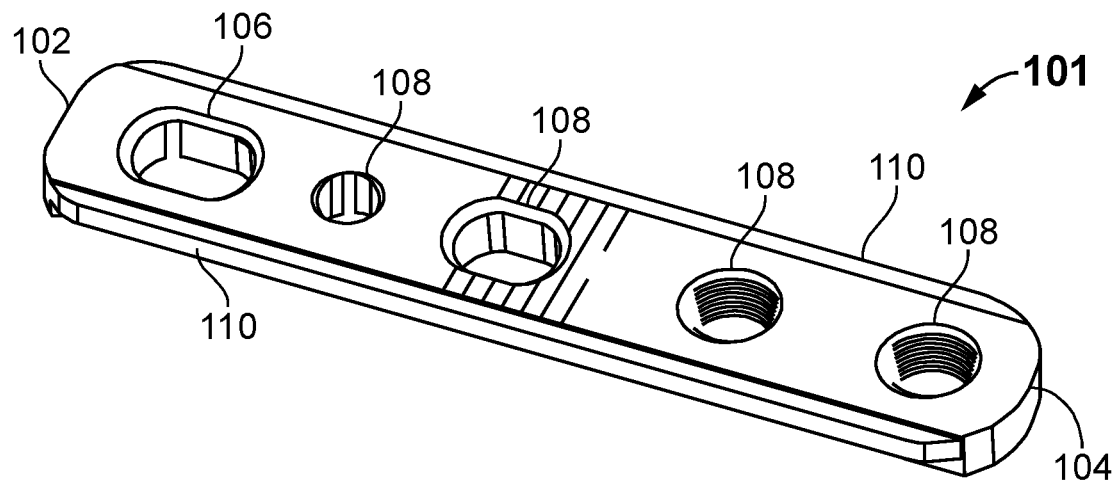
FIG. 2 exemplarily illustrates a perspective view of a first lateral plate, according to an embodiment of the present disclosure.
Figure 3:
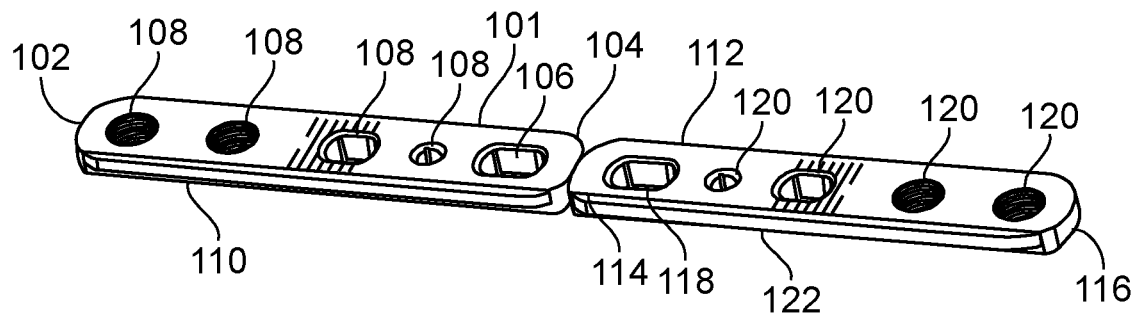
FIG. 3 exemplarily illustrates a perspective view of the first lateral plate and a second lateral plate, according to an embodiment of the present disclosure.

Referring to FIGS. 2-3, a first and second lateral plates (101 and 112) of a surgical kit or a medical device 100 (shown in FIG. 1) used to perform an osteotomy surgery in one embodiment is disclosed. In one embodiment, the lateral plates (101 and 112) could be fixed to the bone 140. Each lateral plate (101 and 112) having a top surface and a bottom surface, wherein the bottom surfaces are to be in contact with the bone 140 when they are implanted. In one embodiment, each lateral plate (101 and 112) comprises a first proximal end 102 and a first distal end 104 and a second proximal end 114 and a second distal end 116, respectively.

The lateral plates (101 and 112) may further comprise one or more through-holes on its surface, configured to affix to the bone 140. In one embodiment, the lateral plates (101 and 112) further comprise at least one compression hole (106 and 118) at the first proximal end 102 second proximal end 114 and one or more locking holes (108 and 120), respectively. In one embodiment, the lateral plates (101 and 112) further comprise a pair of tabs (110 and 122) on both sides, respectively.

In one embodiment, the lateral plates (101 and 112) are fixed on the bone 140 at a distance that is equal to the amount of bone shortening, which is planned before the osteotomy surgery. In one embodiment, the lateral plates (101 and 112) are scaled to allow an accurate amount of osteotomy. In one embodiment, the lateral plates (101 and 112) are scaled by, but not limited to, millimeters. In one embodiment, the locking holes (108 and 120) of the respective lateral plates (101 and 112) include internal threads for enabling a locking relation with a fastening member to affix the lateral plates (101 and 112) to the bone 140.

Figure 4:
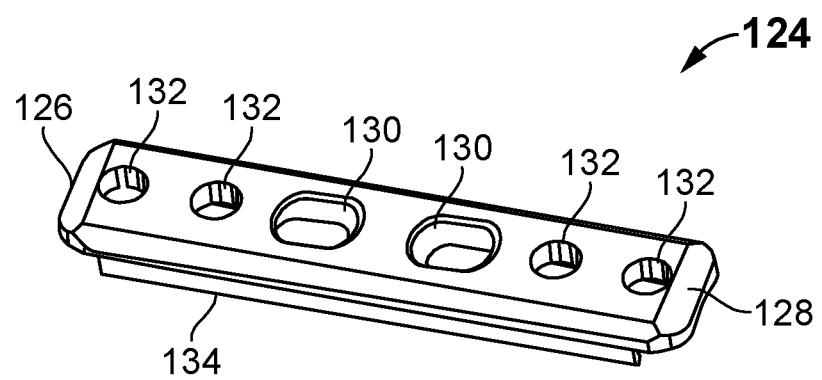
FIG. 4 exemplarily illustrates a perspective view of a central plate, according to an embodiment of the present disclosure.

Referring to FIG. 4, a central plate 124 of the surgical kit or medical device 100 in one embodiment is disclosed. In one embodiment, the central plate 124 having a first end 126 and a second end 128. The central plate 124 is configured to slidably place or affix over the lateral plates (101 and 112) via the first pair of tabs 110 and second pair of tabs 122, respectively, wherein the lateral plates (101 and 112) are fixed to the bone 140 in a distance that is equal to the amount of bone shortening planned before the osteotomy surgery. In one embodiment, the central plate 124 is provided with channels or grooves 134 on both sides.

The central plate 124 could smoothly slide on both lateral plates (101 and 112) via the first pair of tabs 110 and second pair of tabs 122, respectively, thereby exposing the bone between the lateral plates (101 and 112) for enabling the physician or surgeon to precisely perform the osteotomy surgery. In one embodiment, the central plate 124 is also provided with at least two compression holes 130 and one or more through-holes or locking holes 132 having internal threads for securely receiving locking members or fastening members. The internal threads of the locking holes 132 provide a locking relation with the fastening members when the lateral plates (101 and 112) are securely affixed and allows central plate to slide over lateral plates.

In one embodiment, the locking screw in the ends (102, 104, 114, and 116) of lateral plates (101 and 112) is placed to allow the sliding of the central plate 124 on lateral plates (101 and 112) as the locking screw has no prominence head after fixation. The locking screw on the central plate 124 has fixed due to biomechanical issue as the locking screw increases the stability more than the cortical screw. In one embodiment, the cortical screw is fixed on the central plate 124 to achieve the compression in osteotomy site 136 between to pieces of bone 140, to reach early bone union.

Figure 5:
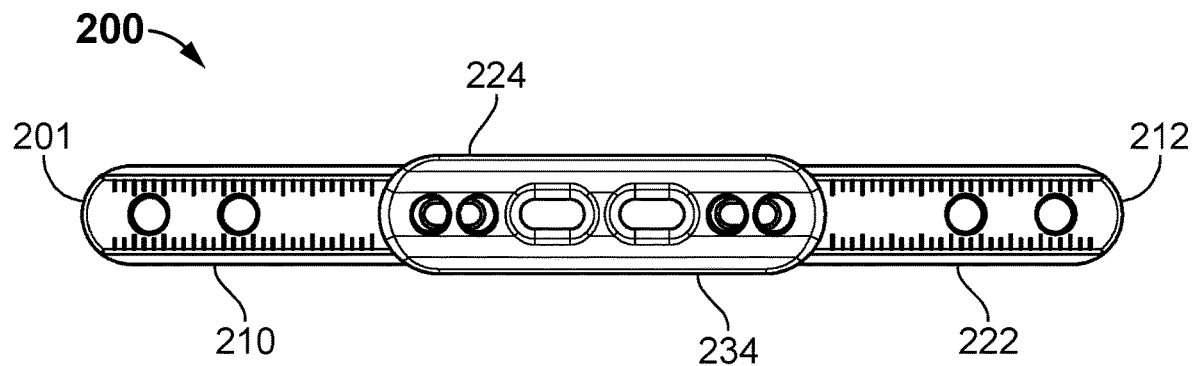
FIG. 5 exemplarily illustrates a top view of a surgical kit or medical device, according to another embodiment of the present disclosure.
Figure 6:
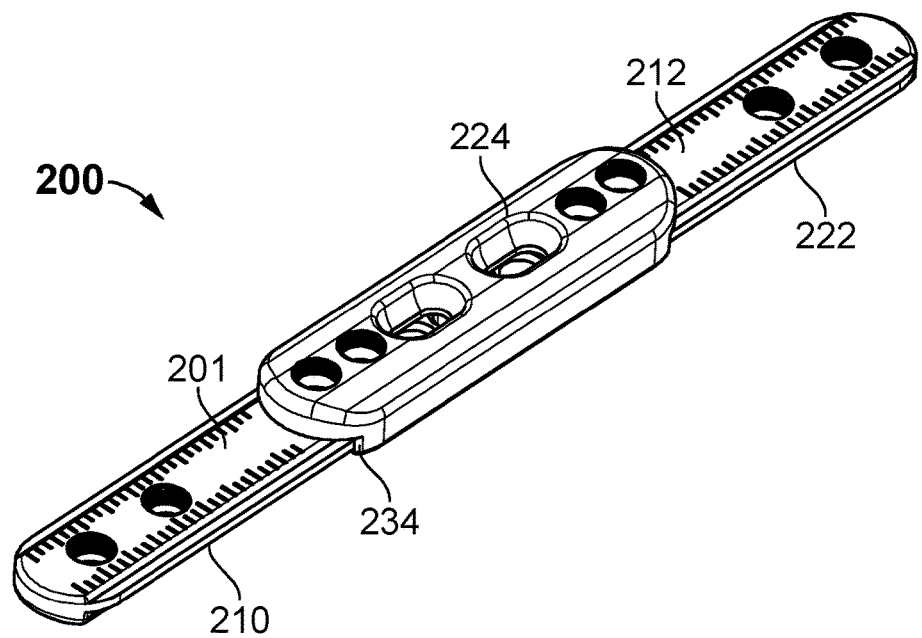
FIG. 6 exemplarily illustrates a perspective view of the surgical device, according to another embodiment of the present disclosure.
Figure 7:
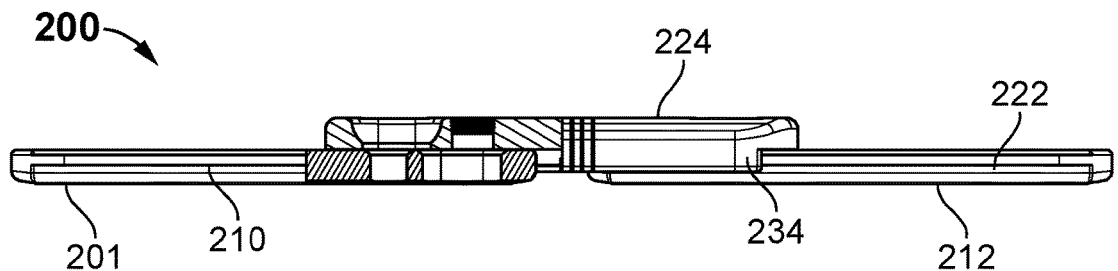
FIG. 7 exemplarily illustrates a side view of the surgical device, according to another embodiment of the present disclosure.

Referring to FIGS. 5-7, different views of a surgical kit or medical device or osteotomy device 200 according to another embodiment is disclosed. In one embodiment, the surgical kit 200 is configured to enable a physician or a surgeon to precisely perform the osteotomy surgery, whereby a bone 140 (shown in FIG. 12) is cut to accurately shorten with maintained anatomical alignment based on pre-osteotomy fixation. In one embodiment, the surgical kit 200 permits the osteotomy with sliding ability to aid in the reduction of complications in a surgical site 136 (shown in FIG. 5) of osteotomy, after plate fixation. In one embodiment, the surgical kit 200 comprises at least two lateral plates and a central plate 224.

The at least two lateral plates include a first lateral plate 201 and a second lateral plate 212. In one embodiment, the central plate 224 is provided with channels or grooves 234 on both sides. In one embodiment, the channels or grooves 234 of the central plate 224 is designed and configured to slide over the lateral plates (201 and 212) via a first pair of tabs or rails 210 and second pair of tabs or rails 222, respectively. In one embodiment, the central plate 224 could be moved to accurately perform the osteotomy surgery for shortening of the bone 140 between the two lateral plates (201 and 212).

Figure 8:
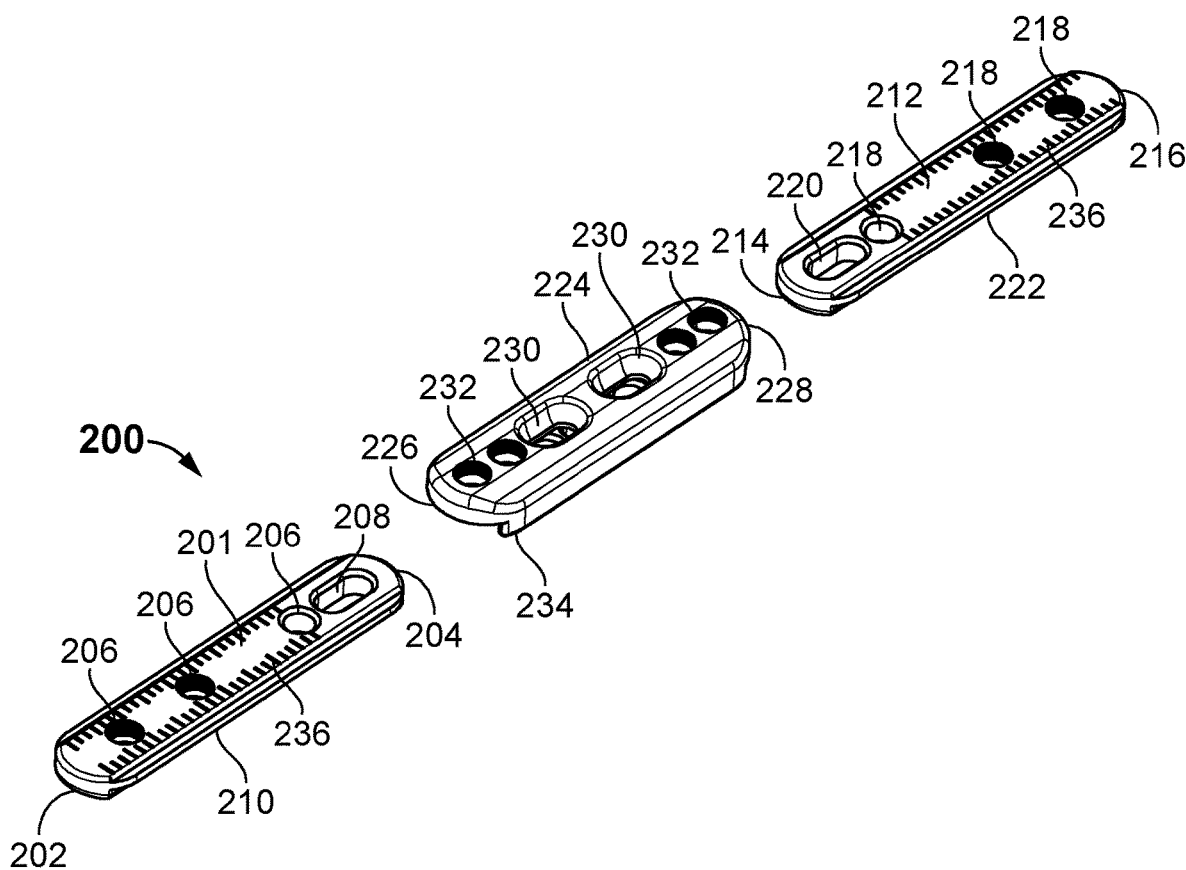
FIG. 8 exemplarily illustrates an exploded view of the surgical device, according to another embodiment of the present disclosure.

Referring to FIG. 8, an exploded view of the surgical kit 200 according to another embodiment is disclosed. In one embodiment, the lateral plates (201 and 212) could be fixed to the bone 140. Each lateral plate (201 and 212) has a dimension of about 50 mm length and 2.22 mm height. Each lateral plate (201 and 212) having a top surface and a bottom surface, wherein the bottom surfaces are to be in contact with the bone 140 when they are implanted. The first lateral plate 201 comprises a first proximal end 204 and a first distal end 202. The second lateral plate 212 comprises a second proximal end 214 and a second distal end 216, respectively.

The lateral plates (201 and 212) may further comprise one or more through-holes on its surface, configured to affix to the bone 140. In one embodiment, the lateral plates (201 and 212) further comprise at least one compression hole (208 and 220) at the first proximal end 204 and second proximal end 214 and one or more locking holes (206 and 218) on their surfaces, respectively. In one embodiment, the locking holes (206 and 218) has a dimension of about 2 mm in radius (4 mm diameter). The adjacent locking holes (206 and 218) are 9 mm apart from each other with respect to the center axis. In one embodiment, the lateral plates (201 and 212) further comprise a pair of tabs (210 and 222) on both sides, respectively. In one embodiment, the locking holes (206 and 218) of the respective lateral plates (201 and 212) include internal threads for enabling a locking relation with a fastening member to affix the lateral plates (201 and 212) to the bone 140.

In one embodiment, the central plate 224 comprises a first end 226 and a second end 228. In one embodiment, the central plate 224 has a dimension of about 45 mm in length, about 3 mm to 3.15 mm in height, and about 12 mm in width. The central plate 224 is configured to slidably place or affix over the lateral plates (201 and 212) via the first pair of tabs 210 and second pair of tabs 222, respectively, wherein the lateral plates (201 and 212) are fixed to the bone 140 in a distance that is equal to the amount of bone shortening planned before the osteotomy surgery. In one embodiment, the central plate 224 is provided with channels or grooves 234 on both sides. In one embodiment, the width of second end 228 is 1.5 mm and width of channels or grooves 234 is 0.5 mm. Length of both is equal to length of central plate 224 which is around 45 mm.

The central plate 224 could smoothly slide on both lateral plates (201 and 212) via the first pair of tabs 210 and second pair of tabs 222, respectively in one embodiment, the central plate 224 is also provided with at least two compression holes 232 and one or more through-holes or locking holes 230 having internal threads for securely receiving locking members or fastening members. In one embodiment, each compression hole 232 has dimension of about 3.5 mm internal diameter (ID) and about 4 mm outer diameter (OD). The internal threads of the locking holes 230 provide a locking relation with the fastening members when the lateral plates (201 and 212) are securely affixed. In one embodiment, the lateral plates (201 and 212) are provided with a scale 236 having measurement lines (laser marked by mm).

In one embodiment, the lateral plates (201 and 212) are fixed on the bone 140 at a distance that is equal to the amount of bone shortening or lengthening, which is planned before the osteotomy surgery. In one embodiment, the lateral plates (201 and 212) are scaled to allow an accurate amount of osteotomy, while the central plate 224 is positioned over the two lateral plates (201 and 212) to read the scale 236 provided on the central plate 224. In one embodiment, the central plate 224 is positioned over the two lateral plates (201 and 212) to maintain the alignment between two lateral plates (201 and 212). In one embodiment, the lateral plates (201 and 212) are scaled by, but not limited to, millimeters.

In one embodiment, the locking screw in the ends (202, 204, 214, and 216) of lateral plates (201 and 212) is placed to allow the sliding of the central plate 224 on lateral plates (201 and 212) as the locking screw has no prominence head after fixation. The locking screw on the central plate 224 has fixed due to bio-mechanical issue as the locking screw increases the stability more than the cortical screw. In one embodiment, the cortical screw is fixed on the central plate 224 (before locking screws) to achieve the compression in osteotomy site 136 between to pieces of bone 140, to reach early bone union.

Figure 9:
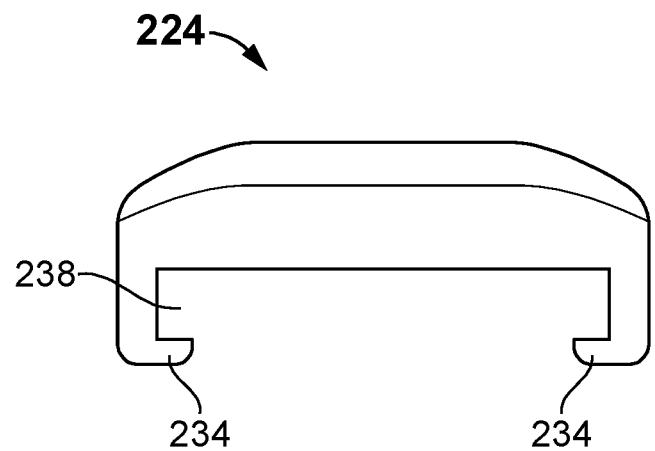
FIG. 9 exemplarily illustrates an end view of a lateral plate, according to another embodiment of the present disclosure.

Referring to FIG. 9, an end view of the central plate 224 according to another embodiment is disclosed. In one embodiment, the central plate 224 is provided with channels or grooves 234 along the length of the central plate 224 on both sides. In one embodiment, the channels or grooves 234 of the central plate 224 is designed to provide a space or gap 238 to snugly slide over the lateral plates (201 and 212).

Figure 10:
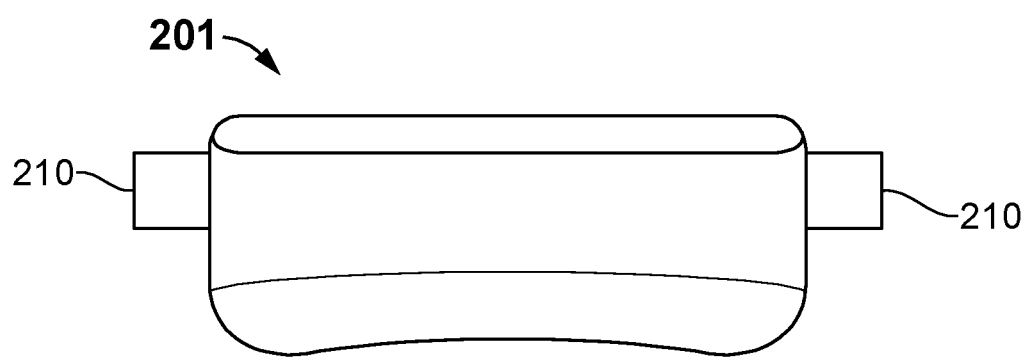
FIG. 10 exemplarily illustrates an end view of a central plate, according to another embodiment of the present disclosure.

Referring to FIG. 10, an end view of at least one lateral plate 201 according to another embodiment is disclosed. In one embodiment, the lateral plate 201 comprises a pair of tabs 210 along the length of the lateral plate 201 on both sides. The pair of tabs 210 are snugly positioned into the grooves 234 configured to allow the central plate 224 to slide along its length.

Figure 11:
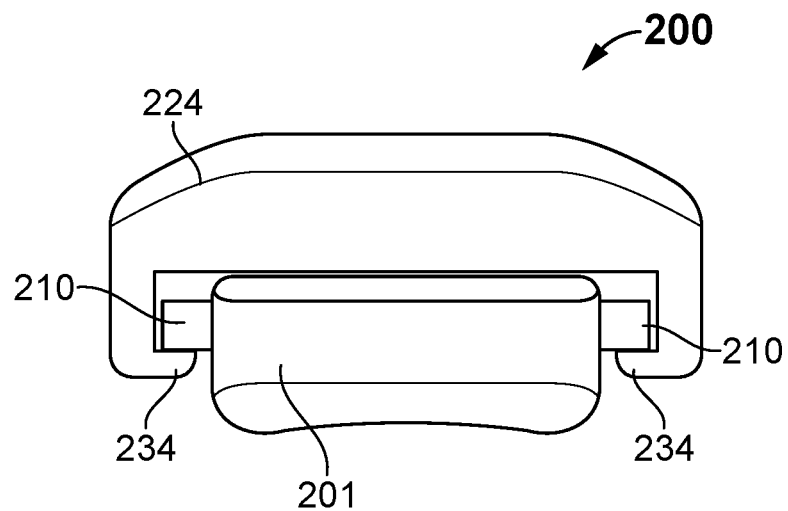
FIG. 11 exemplarily illustrates an end view of the surgical device, according to another embodiment of the present disclosure.

Referring to FIG. 11, an end view of the surgical kit 200 according to another embodiment is disclosed. The pair of tabs 210 of the lateral plate 201 is positioned into the space 238 created by the grooves 234, thereby allowing the central plate 224 to slide over the lateral plate 201 in the osteotomy site via a first pair of tabs 210. In one embodiment, this arrangement can be placed in either ulnar or radius bone or any other long bones. For any distal metaphyseal radial shortening, one of the lateral plates 201 is designed in T shape so, the central plate 224 can slides on the straight lateral plate. The design configuration allows the surgeon to perform shortening osteotomy in more distal part of radius bone.

One aspect of the present disclosure is directed to a surgical kit for performing an osteotomy. The surgical kit comprises at least two lateral plates, including a first lateral plate fixed over a bone having a top surface configured to face away from the bone when implanted, a bottom surface configured to be in contact with the bone when implanted, a first proximal end and a first distal end aligned along a longitudinal axis of the bone, wherein the first lateral plate has one or more through-holes on its surface configured to fix to the bone. The at least two lateral plates may further include a second lateral plate fixed over the bone adjacent to the first lateral plate having a top surface configured to face away from the bone when implanted, a bottom surface configured to be in contact with the bone when implanted, a second proximal end and a second distal end aligned along a longitudinal axis of the bone. The second lateral plate may have one or more through-holes on its surface configured to fix to the bone.

The surgical kit further comprises a central plate slidably placed over the first lateral plate and the second lateral plate, wherein the central plate has a top surface configured to face away from the at least two lateral plates when implanted, a bottom surface configured to be in contact with the at least two lateral plates when implanted, a first end and a second end aligned along a longitudinal axis of the bone. The central plate may have one or more through-holes on its surface configured to securely fix the osteotomy site and at least two lateral plates to the bone via one or more fasteners, thereby allowing an accurate amount of bone shortening and anatomical reduction and fixation of osteotomy site.

Figure 12:
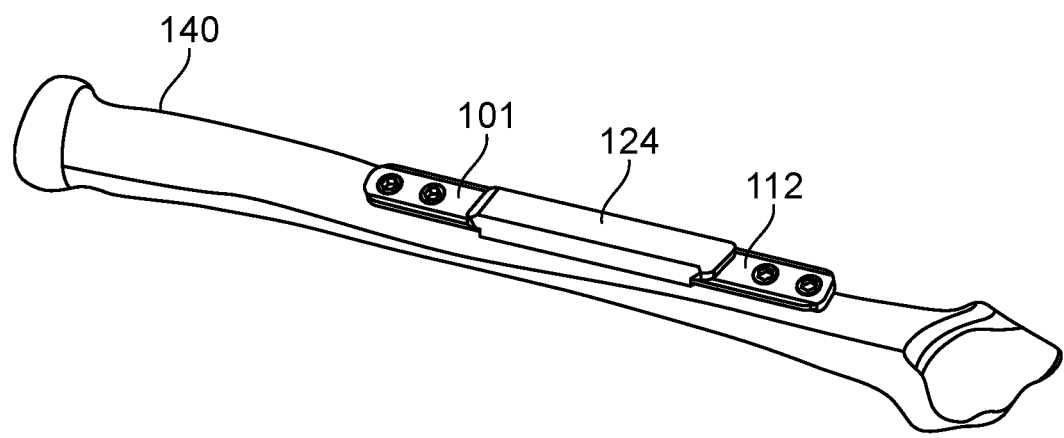
FIG. 12 exemplarily illustrates the lateral plates affixed to a surgical site, according to an embodiment of the present disclosure.

Referring to FIG. 12, the lateral plates (101 and 112) affixed to the surgical site or shortening osteotomy site 136 of the Radius bone 140 according to one embodiment is disclosed. In one embodiment, the lateral plates (101 and 112) are securely affixed or placed at a proper distance on the surgical site or shortening osteotomy site 136 of the bone, for example, radius bone 140 or any other long bone while central plate is over them to keep the anatomical alignment. The distance between two fixed lateral plates is equal to the shortening amount based on the pre-operative plan. This distance is between the first proximal and second proximal end of the first and second lateral plates. In one embodiment, the lateral plates (101 and 112) are affixed to the Radius bone 140 using at least, but not limited to, four locking screws, i.e., two screws in each lateral plate (101 and 112) via the locking holes (108 and 120), respectively, thereby exposing the surgical site 136 of the Radius bone 140 is achieved by sliding the central bone laterally. The lateral plates (101 and 112) are scaled by millimeters.

Figure 13:
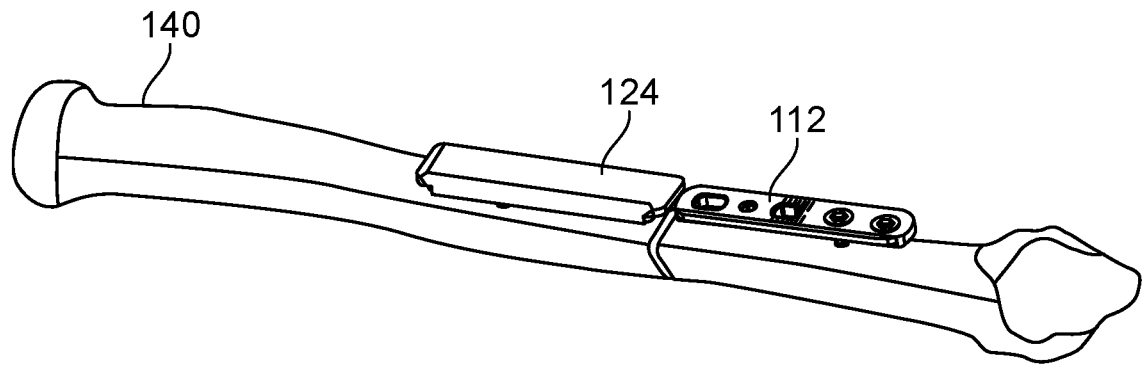
FIG. 13 exemplarily illustrates a shortening osteotomy in the surgical site, according to an embodiment of the present disclosure.
Figure 14:
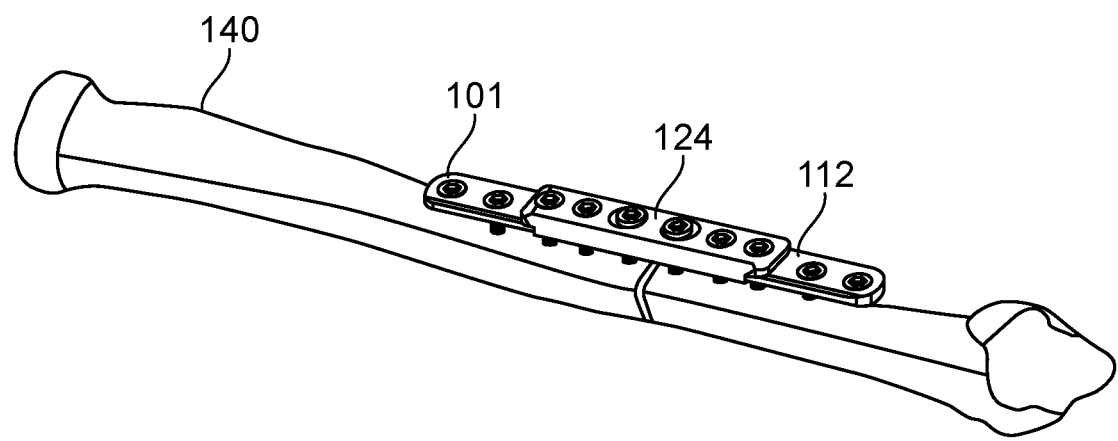
FIG. 14 exemplarily illustrates the central plate and the lateral plates affixed to the surgical site, according to an embodiment of the present disclosure.

Referring to FIGS. 13-14, a shortening osteotomy by cutting away a part of the bone 140 between the lateral plates (101 and 112) in one embodiment is disclosed (two parallel bone cut). The two lateral plates (101 and 112) which were placed at an exact distance, which was equal to the shortening amount based on the pre-operative plan. After osteotomy and removing the bone cut, will stick together longitudinally without any distance between them, then central plate slides over lateral plates and covers the osteotomy site and results in anatomical reduction. In one embodiment, the central plate 124 is slidably positioned over the lateral plates (101 and 112) via the first pair of tabs 110 and second pair of tabs 122, respectively. The central plate 124 slides laterally, thereby exposing the surgical site 136 of the radius bone 140. The radius bone 140 could be one of the forearm bones. The forearm bones consist of the ulnar bone and the radius bone. Further, at another step, the osteotomy could be performed equal to the distance between the lateral plates (101 and 112) as shown in FIG. 13.

The first lateral plate may further comprise at least one locking hole at the first proximal end and one or more locking holes at the first distal end. The first lateral plate may, in one example, comprise a first pair of tabs on both sides along its length. The second lateral plate includes at least one compression hole at the second proximal end and one or more locking holes at the second distal end. The second lateral plate may include a second pair of tabs on both sides along its length. The central plate may, in one example, include at least two compression holes at its center and one or more locking holes proximal to the compression holes.

The central plate further comprises a channel on both sides along its length configured to slide laterally along the tabs of the at least two lateral plates. The first lateral plate and the second lateral plate are scaled and fixed on the bone with exact distance based on a pre-operative plan. The exact distance may be measured by the scaled lateral plates. The distance between the first lateral plate and the second lateral plate is, in one example, equal to the shortening amount of bone based on the pre-operative measurements. The holes of the central plate and the at least two lateral plates may be superimposed for final fixation. The one or more fasteners may be at least two cortical screws and one or more locking screws.

Figure 15:
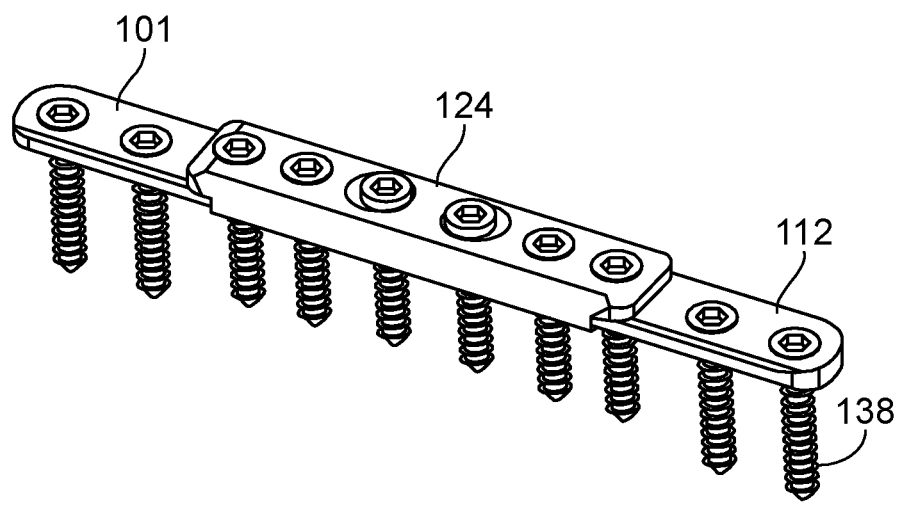
FIG. 15 exemplarily illustrates one or more locking screws configured to mount the central plate and the lateral plates to the surgical site, according to an embodiment of the present disclosure.

Referring to FIG. 15, one or more fasteners configured to mount the central plate 124 and the lateral plates (101 and 112) to the surgical site 136 of the bone 140, according to an embodiment of the present disclosure. During the final fixation, the osteotomy plates (101, 112, and 124) are positioned over the bone 140 and affixed using one or more fasteners 138. In one embodiment, the one or more fasteners 138 are at least two cortical screws and one or more locking screws.

Furthermore, the central plate 124 could slide on the lateral slides (101 and 112) in osteotomy site 136. The central plate 124 is fixed to the bone 140 using at least two screws, for example, cortical screws via the compression holes 130 (shown in FIG. 4) and then the locking screws will be fixed through the locking holes (108, 120, and 132) and compression holes (106, 118, and 130) as shown in FIG. 15. It is crucial that the plate holes of central plate 124 and two lateral plates (101 and 112) will be only superimposed when there is no distance or gap between the two lateral plates (101 and 112). It is clear that, the osteotomy reduction will be anatomical based on sliding slut, which is in plates and there will be just one way to reduce the osteotomy site 136.

Figure 16:
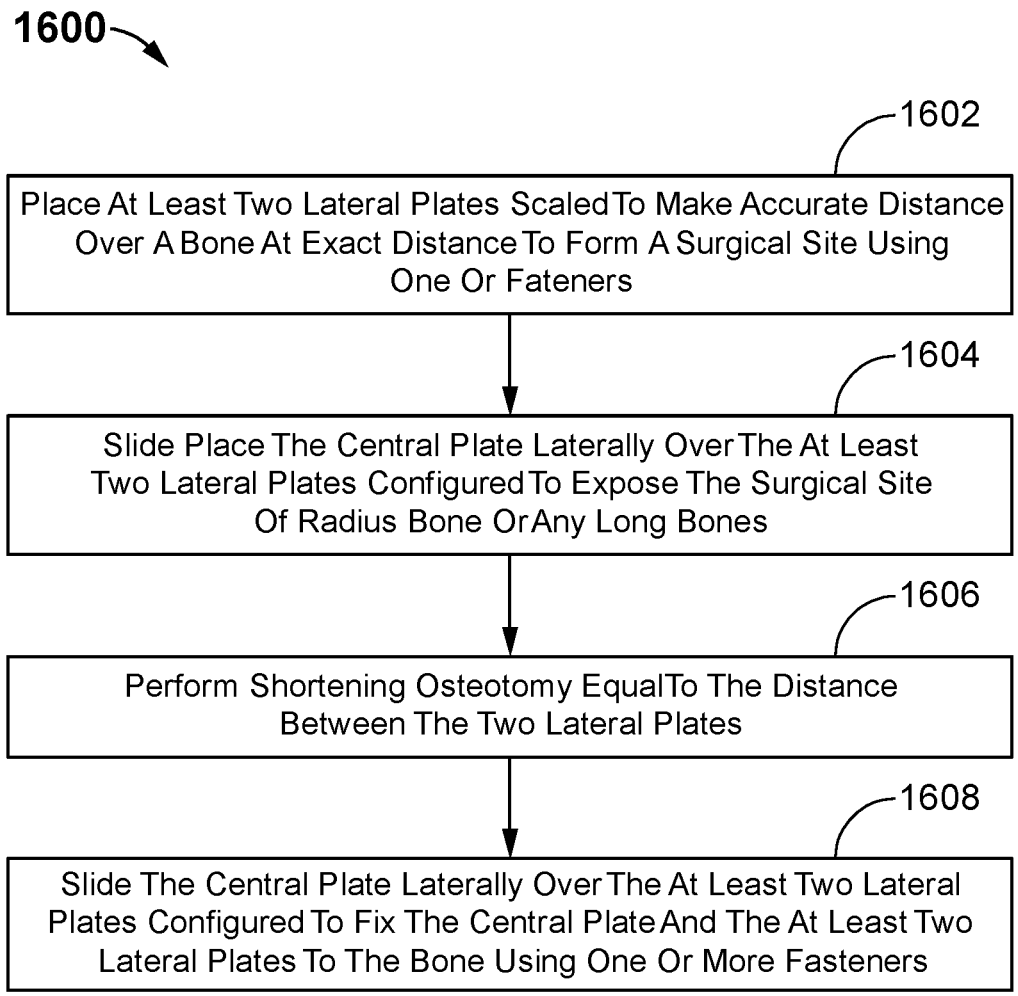
FIG. 16 exemplarily illustrates a method for performing osteotomy, according to an embodiment of the present disclosure.

Referring to FIG. 16, a method 1600 for performing osteotomy is disclosed, according to one embodiment of the present disclosure. In one embodiment, the present disclosure follows the method 1600 for performing osteotomy using surgical kit 100 having at least two lateral plates and a central plate 124. In one embodiment, the at least two lateral plates include a first lateral plate 101 and a second lateral plate 112. In one embodiment, the two lateral plates (101 and 112) are adjacently fixed over a bone 140 at a pre-defined distance 136. In one embodiment, the central plate is slidably placed over the two lateral plates (101 and 112) configured to securely fix the two lateral plates (101 and 112) to the bone 140 via one or more fasteners 138.

In one embodiment, the method 1600 follows the following steps. At step 1602, the two lateral plates (101 and 112) scaled to make accurate distance are placed over the bone 140 at exact distance to form a surgical site 136. In one embodiment, the at least two lateral plates (101 and 112) are fixed to the bone 140 via one or more locking holes using one or more fasteners 138. In one embodiment, the first lateral plate 101 has at least two locking holes 108 at a first distal end 102 and the second lateral plate 112 has at least two locking holes 120 at a second distal end 116. In one embodiment, the fasteners 138 could be one or more cortical screw and one or more locking screws. In one embodiment, the at least two lateral plates (101 and 112) are fixed to the bone 140 while the central plate 124 is positioned over the two lateral plates (101 and 112) to read the scale. In one embodiment, the central plate 124 is positioned over the two lateral plates (101 and 112) to maintain the alignment between two lateral plates (101 and 112).

At step 1604, the central plate 124 slides over the two lateral plates (101 and 112). In one embodiment, the central plate 124 slides laterally configured to expose the surgical site 136 of Radius bone 140 or any long bone. At step 1606, the surgical bone 140 is shortened equal to the distance between the two lateral plates (101 and 112) using the shortening osteotomy process. In one embodiment, the distance between the first lateral plate 101 and the second lateral plate 112 is equal to the shortening amount of bone based on the pre-operative measurements. In one embodiment, the method 1600 could also be used to lengthen the surgical bone 140.

At step 1608, the central plate 124 slides laterally over the two lateral plates (101 and 112) in the osteotomy site 136 configured to fix the central plate 124 and the two lateral plates (101 and 112) to the bone 140 using one or more fasteners 138 by aligning the holes (106, 108, 118, 120, 130, and 132) of central plate 124 and the two lateral plates (101 and 112). In one embodiment, the holes (130 and 132) of central plate 124 and the holes (106, 108, 118, and 120) of the two lateral plates (101 and 112) are superimposed for final fixation to the bone 140 using one or more fasteners 138. In one embodiment, the one or more fasteners 138 are at least two cortical screws and one or more locking screws. In one embodiment, the compression holes (106 and 118) of the lateral plates (101 and 112) are aligned to the compression holes 130 of the central plate 124. In one embodiment, the locking holes (108 and 120) of the two lateral plates (101 and 112) are aligned to the locking holes 132 of the central plate 124.

Another aspect of the present disclosure is directed to a method of performing osteotomy using a surgical kit having at least two lateral plates that include a first lateral plate and a second lateral plate, adjacently fixed over a bone at a pre-defined distance and a central plate slidably placed over the at least two lateral plates configured to securely fix the at least two lateral plates to the bone using one or more fasteners. The method includes placing the at least two lateral plates over a bone at exact distance to form a surgical site while the central plate is over them, wherein the at least two lateral plates are fixed to the bone via one or more locking holes using one or more fasteners. The method further comprises sliding the central plate laterally over the at least two lateral plates configured to expose the surgical site of radius bone or any long bone; and performing shortening osteotomy equal to the distance between the two lateral plates. Moreover, the method may further include sliding the central plate laterally over the at least two lateral plates in the osteotomy site configured to fix the central plate and the at least two lateral plates to the bone using one or more fasteners by aligning the holes of the central plate and the at least two lateral plates.

The first lateral plate may have at least two locking holes at a first distal end and the second lateral plate may have at least two locking holes at a second distal end. The distance between the first lateral plate and the second lateral plate may be equal to the shortening amount of bone based on the pre-operative measurements. The central plate is able to slide over the first lateral plate and the second lateral plate, thereby allowing an accurate amount of bone shortening and anatomical reduction and fixation of osteotomy site. Moreover, the holes of the central plate and the at least two lateral plates are able to be superimposed for final fixation.

Figure 17:
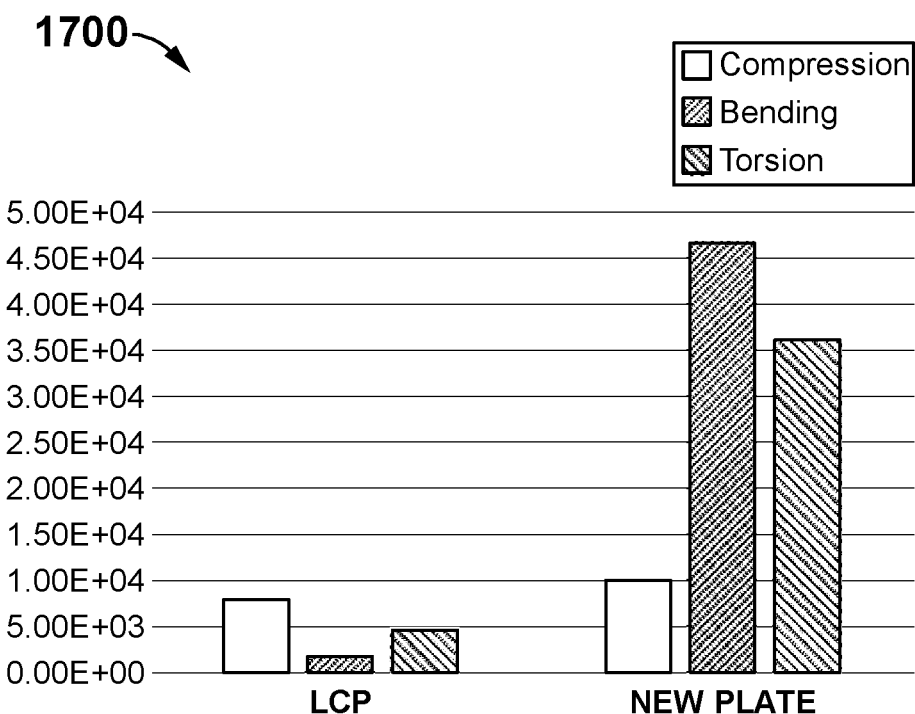
FIG. 17 exemplarily illustrates a graph demonstrating a model stiffness analysis in comparison with 6 holes 3.5 conventional limited contact dynamic compression plate (LC-DCP) on radius bone, according to an embodiment of the present disclosure.

Referring to FIG. 17, a graph 1700 demonstrating model stiffness analysis of finite element analysis is disclosed, according to one embodiment of the present disclosure. The graph 1700 compares the features such as compression, bending, and torsion of the conventional 6 holes DCP plate and the new plate (sliding plate). The model stiffness analysis determines the improved functionalities with respect to stiffness, displacement and stress of the conventional 6 holes DCP plate and the new plate. The result of the model stiffness analysis shows that the new plate functions better than the conventional 6 holes DCP plate with respect to the factors such as compression, bending, and torsion.

Figure 18:
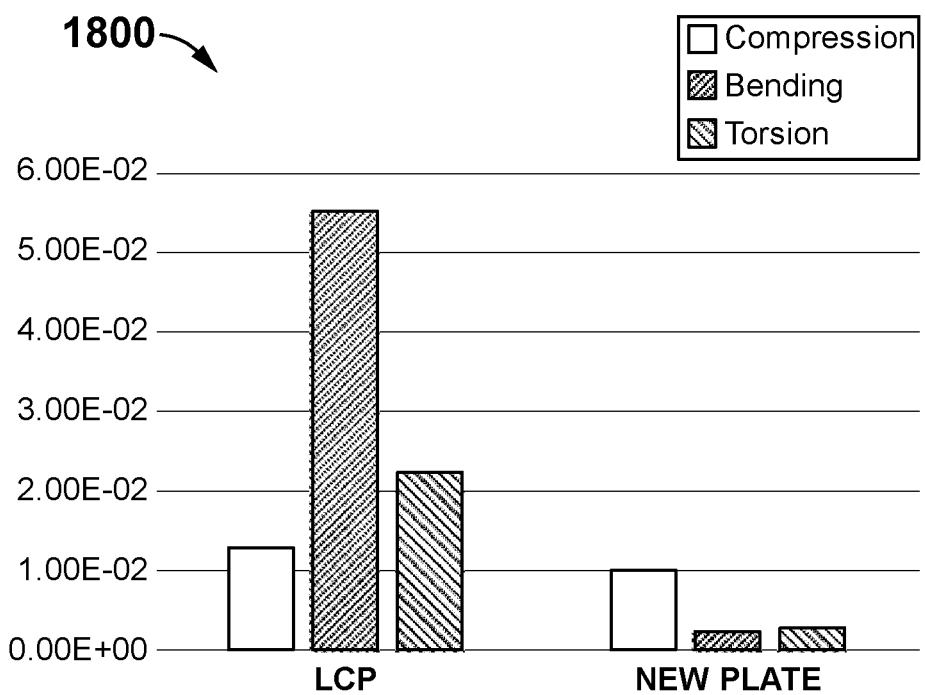
FIG. 18 exemplarily illustrates a graph demonstrating a bone displacement analysis in comparison with 6 holes 3.5 conventional limited contact dynamic compression plate (LC-DCP) on radius bone, according to an embodiment of the present disclosure.

Referring to FIG. 18, a graph 1800 demonstrating bone displacement while using the conventional 6 holes DCP plate and the new plate is disclosed, according to one embodiment of the present disclosure. The graph 1800 compares the features such as compression, bending, and torsion of the conventional 6 holes DCP plate and the new plate. The bone displacement analysis determines the improved functionalities with respect to stiffness, displacement and stress of the conventional 6 holes DCP plate and the new plate. The result of the bone displacement analysis shows that the new plate reduces bone displacement than the conventional 6 holes DCP plate with respect to the factors such as compression, bending, and torsion.

Figure 19:
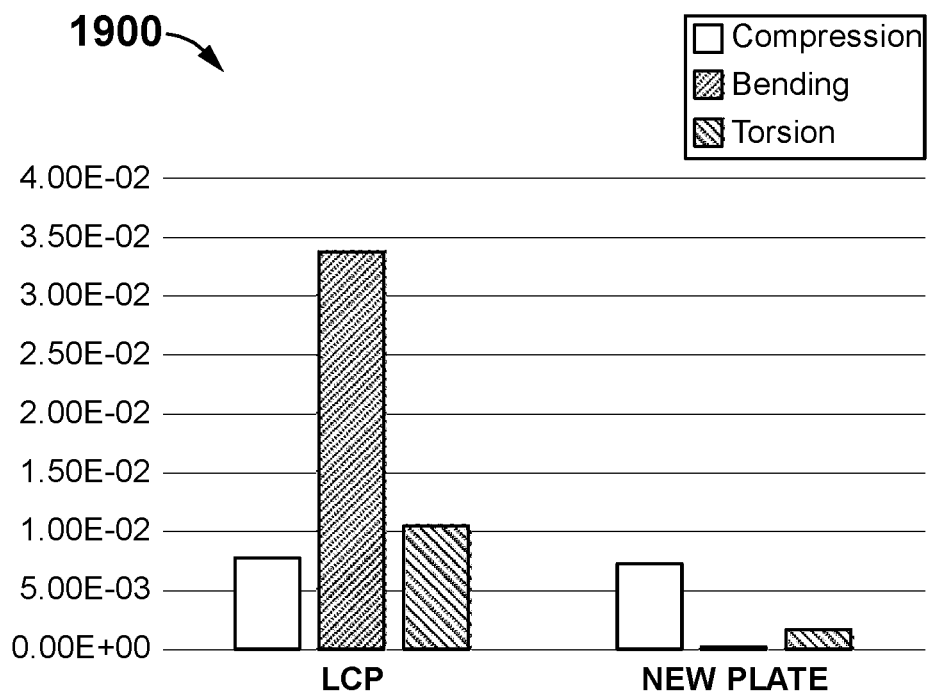
FIG. 19 exemplarily illustrates a graph demonstrating a plate displacement analysis in comparison with 6 holes 3.5 conventional limited contact dynamic compression plate (LC-DCP) on radius bone, according to an embodiment of the present disclosure.

Referring to FIG. 19, a graph 1900 demonstrating a comparison chart for plate displacement analysis between the conventional 6 holes DCP plate and the new plate, according to one embodiment of the present disclosure. The graph 1900 compares the features such as compression, bending, and torsion of the conventional 6 holes DCP plate and the new plate to determine the plate displacement. The plate displacement analysis determines the improved functionalities with respect to stiffness, displacement and stress of the conventional 6 holes DCP plate and the new plate. The result of the plate displacement analysis clearly shows that the new plate has reduced plate displacement when compared to the conventional 6 holes DCP plate with respect to the factors such as compression, bending, and torsion.

Figure 20:
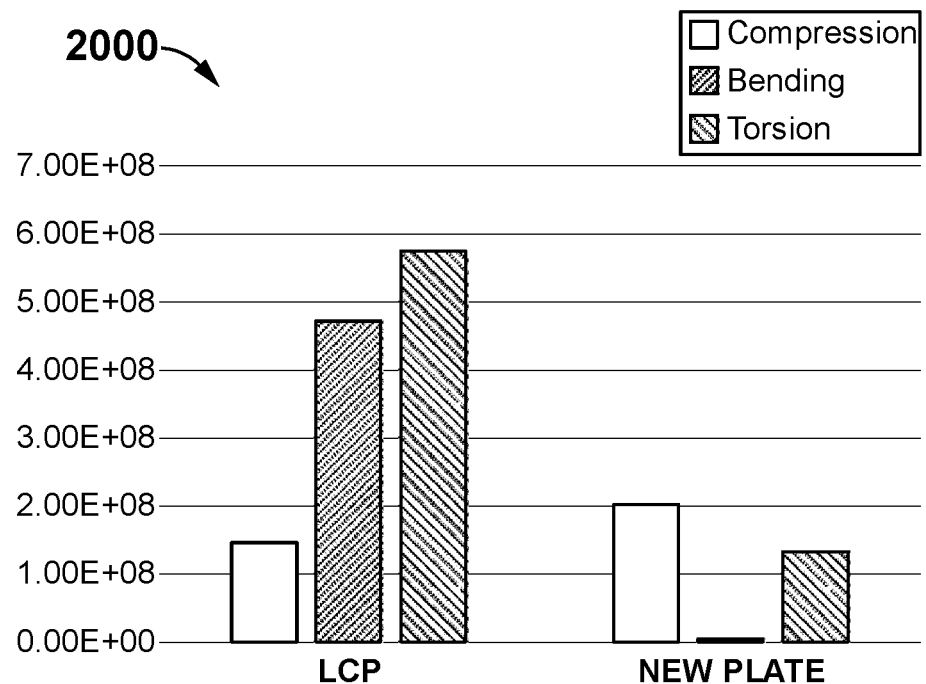
FIG. 20 exemplarily illustrates a graph demonstrating a bone stress analysis in comparison with 6 holes 3.5 conventional limited contact dynamic compression plate (LC-DCP) on radius bone, according to an embodiment of the present disclosure.

Referring to FIG. 20, a graph 2000 demonstrating a comparison chart for bone stress analysis between conventional 6 holes DCP plate and the new plate, according to one embodiment of the present disclosure. The graph 2000 compares the features such as compression, bending, and torsion of the conventional 6 holes DCP plate and new plate to determine the bone stress. The bone stress analysis determines the improved functionalities with respect to stiffness, displacement and stress of the conventional 6 holes DCP plate and new plate. The result of the bone stress analysis clearly shows that the new plate has reduced bone stress when compared to the conventional 6 holes DCP plate with respect to the factors such as compression, bending, and torsion.

Figure 21:
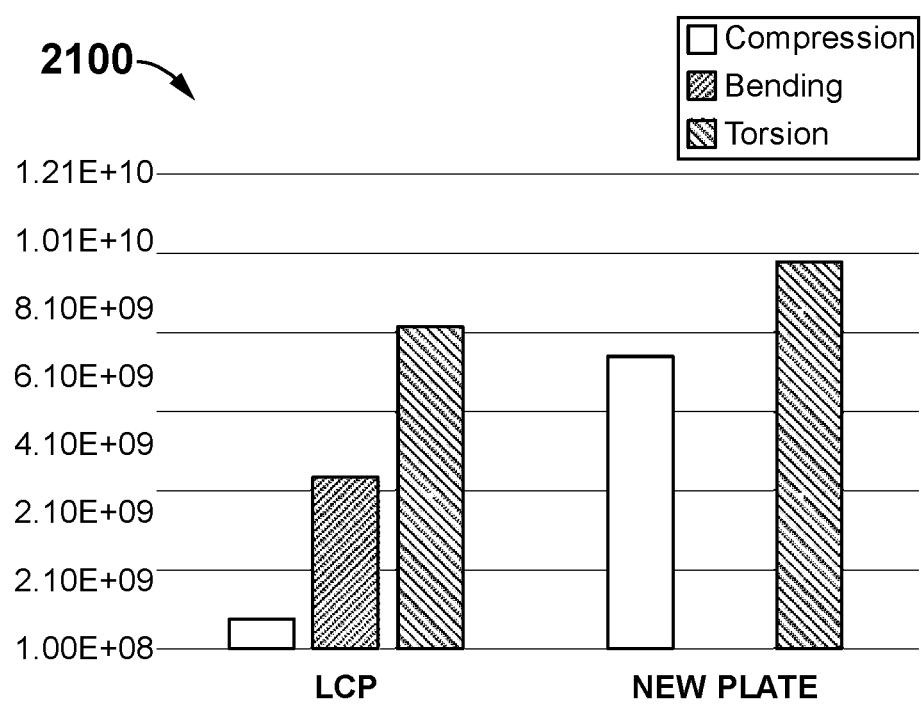
FIG. 21 exemplarily illustrates a graph demonstrating a plate stress analysis in comparison with 6 holes 3.5 conventional limited contact dynamic compression plate (LC-DCP) on radius bone, according to an embodiment of the present disclosure.

Referring to FIG. 21, a graph 2100 demonstrating a comparison chart for plate stress analysis between DCP and the new plate, according to one embodiment of the present disclosure. The graph 2100 has plotted to compare the features such as compression, bending, and torsion of the conventional 6 holes DCP plate and new plate to determine the plate stress. The plate stress analysis determines the improved functionalities with respect to stiffness, displacement and stress of conventional 6 holes DCP plate and new plate. The result of the plate stress analysis clearly shows that the new plate has considerable plate stress when compared to the conventional 6 holes DCP plate with respect to the factors such as compression and torsion.

Advantageously, the surgical kit of the present disclosure allows exact and accurate amount of shortening of the bone. Also, the surgical kit enables anatomical reduction and fixation of osteotomy site using the sliding ability of plates, which allows before-osteotomy fixation. Therefore, the surgeon could perform the osteotomy for shortening the bone with the best accuracy. The surgical kit reduces the complication such as malunion in osteotomy site. In addition, the surgical kit reduces complications such as rotational and angular malreduction. The surgical kit increases the accuracy of the length of shortening by accurate matching of osteotomy and decreases the surgical time. Prevention of over shortening osteotomy which is a common complication. This surgical kit also reduces the surgical time because by before-osteotomy fixation, time for anatomic reduction will be saved. Reduction in the surgical time also reduces the rate of possible surgical site infection and surgical cost.

The foregoing description comprise illustrative embodiments of the present disclosure. Having thus described exemplary embodiments of the present disclosure, it should be noted by those skilled in the art that the within disclosures are exemplary only, and that various other alternatives, adaptations, and modifications may be made within the scope of the present disclosure. Merely listing or numbering the steps of a method in a certain order does not constitute any limitation on the order of the steps of that method.

Many modifications and other embodiments of the disclosure will come to mind to one skilled in the art to which this disclosure pertains having the benefit of the teachings presented in the foregoing descriptions. Although specific terms may be employed herein, they are used only in generic and descriptive sense and not for purposes of limitation. Accordingly, the present disclosure is not limited to the specific embodiments illustrated herein. While the above is a complete description of the preferred embodiments of the disclosure, various alternatives, modifications, and equivalents may be used. Therefore, the above description and the examples should not be taken as limiting the scope of the disclosure, which is defined by the appended claims.

The invention claimed is:

1. A surgical kit for performing osteotomy, comprising:
at least two lateral plates that include
a first lateral plate adapted to have a top surface configured to face away from a bone when implanted, a bottom surface configured to be in contact with the bone when implanted, a first proximal end and a first distal end aligned along a longitudinal axis of the bone, wherein the first lateral plate has one or more through-holes on its surface configured to fix to the bone,
a second lateral plate fixed over the bone adjacent to the first lateral plate having a top surface configured to face away from the bone when implanted, a bottom surface configured to be in contact with the bone when implanted, a second proximal end and a second distal end aligned along a longitudinal axis of the bone, wherein the second lateral plate has one or more through-holes on its surface configured to fix to the bone;
a central plate slidably placed over the first lateral plate and the second lateral plate, wherein the central plate has a top surface configured to face away from the at least two lateral plates when implanted, a bottom surface configured to be in contact with the at least two lateral plates when implanted, a first end and a second end aligned along a longitudinal axis of the bone, and wherein the central plate further comprises at least two compression holes at its center and one or more locking holes proximal to the compression holes,
wherein the two lateral plates are configured to be fixed on a bone in anatomical alignment by the central plate, and the central plate is placed on the two lateral plates, thereby allowing the fixed lateral plates to preserve the anatomical alignment and measure the exact distance between two lateral plates, the distance between the two lateral plates is adapted to the amount of shortening osteotomy,
wherein the central plate has one or more through-holes on its surface configured to securely fix the at least two lateral plates to the bone at an exact distance equal to the amount of bone shortening osteotomy via one or more fasteners, thereby allowing an accurate amount of bone shortening and anatomical reduction and fixation of osteotomy site.

2. The surgical kit of claim 1, wherein the first lateral plate further comprises one or more locking holes at the first distal end.

3. The surgical kit of claim 1, wherein the first lateral plate further comprises a first pair of tabs on both sides along its length.

4. The surgical kit of claim 1, wherein the second lateral plate further comprises one or more locking holes at the second distal end.

5. The surgical kit of claim 1, wherein the second lateral plate further comprises a pair of tabs on both sides along its length.

6. The surgical kit of claim 1, wherein the central plate further comprises a channel on both sides along its length configured to slide laterally along a pair of tabs of the at least two lateral plates.

7. The surgical kit of claim 1, wherein the first lateral plate and the second lateral plate are scaled and configured to be fixed on a bone with exact distance based on a pre-operative plan and the exact distance is measured by the scaled lateral plates.

8. The surgical kit of claim 1, wherein the distance between the first lateral plate and the second lateral plate is configured equal to the shortening amount of a bone based on the pre-operative measurements.

9. The surgical kit of claim 1, wherein the holes of the central plate and the at least two lateral plates are superimposed for final fixation.

10. The surgical kit of claim 1, wherein the one or more fasteners are at least two cortical screws and one or more locking screws.

* * * * *